US009155606B2

(12) United States Patent
Benoit et al.

(10) Patent No.: US 9,155,606 B2
(45) Date of Patent: Oct. 13, 2015

(54) METHOD AND APPARATUS FOR REHYDRATION OF LYOPHILIZED BIOLOGIC MATERIALS (75) Inventors: Bethanie J. Benoit, North Smithfield, RI (US); Karen Elizabeth Kullas, Berkley, MA (US); Devang Vijay Shah, Wrentham, MA (US)

(73) Assignee: C. R. BARD, INC., Murray Hill, NJ (US)

( * ) Notice: Subject to any disclaimer, the term of this patent is extended or adjusted under 35 U.S.C. 154(b) by 0 days.

(21) Appl. No.: 13/424,794

(22) Filed: Mar. 20, 2012

(65) Prior Publication Data

US 2013/0248386 A1 Sep. 26, 2013

(51) Int. Cl.
| A61F 2/00 | (2006.01) |
| A61J 1/10 | (2006.01) |
| A61J 1/20 | (2006.01) |
| B65D 30/24 | (2006.01) |
| B65D 75/58 | (2006.01) |
| B65D 77/04 | (2006.01) |

(52) U.S. Cl.
CPC .......... *A61F 2/0095* (2013.01); *A61J 1/10* (2013.01); *A61J 1/2096* (2013.01); *B65D 31/147* (2013.01); *B65D 75/5855* (2013.01); *B65D 77/04* (2013.01); *A61F 2/0063* (2013.01)

(58) Field of Classification Search
USPC ................................................ 206/205, 438
See application file for complete search history.

(56) References Cited

U.S. PATENT DOCUMENTS

| 2,902,146 | A | * | 9/1959 | Doherty | 206/361 |
| 3,043,067 | A | * | 7/1962 | Rynkiewicz et al. | 53/426 |
| 3,315,802 | A | * | 4/1967 | Lonholdt et al. | 206/205 |
| 3,326,450 | A | * | 6/1967 | Langdon | 206/438 |
| 3,342,326 | A | * | 9/1967 | Zackheim | 222/211 |
| 4,176,746 | A | * | 12/1979 | Kooi | 206/438 |
| 4,197,947 | A | * | 4/1980 | Zaidi | 206/438 |
| 4,467,588 | A | | 8/1984 | Carveth | |
| 4,511,533 | A | * | 4/1985 | Guadagno et al. | 422/413 |
| 4,537,305 | A | * | 8/1985 | Takanashi | 206/438 |
| 4,557,381 | A | * | 12/1985 | Whitney | 206/440 |
| 4,597,765 | A | * | 7/1986 | Klatt | 623/23.67 |
| 5,031,762 | A | * | 7/1991 | Heacox | 206/210 |
| 5,217,118 | A | * | 6/1993 | Mochizuki et al. | 206/524.2 |
| 5,392,918 | A | * | 2/1995 | Harrison | 206/571 |
| 5,549,388 | A | * | 8/1996 | Wilkes | 383/84 |

(Continued)

FOREIGN PATENT DOCUMENTS

WO 02/16209 A1 2/2002

*Primary Examiner* — Anthony Stashick
*Assistant Examiner* — Mollie Llewellyn
(74) *Attorney, Agent, or Firm* — Saul Ewing LLP (57) ABSTRACT The present invention is a method and an apparatus for packaging lyophilized implants and other medical devices. In accordance with the invention, a lyophilized implant may be packaged for delivery to the surgical site in a sealed, flexible/expandable, sterile inner pouch. The inner pouch may be further packaged within an outer, sterile package. The inner pouch contains a resealable port through which rehydration liquid may be introduced into the inner pouch without opening the inner pouch. The inner pouch may be made of a flexible, substantially non-stretchable material so that the pouch can expand only to a predetermined maximum size to accept a predetermined volume of rehydration liquid. After rehydration, any excess rehydration liquid within the pouch may be removed via the same port. Next, the pouch is opened via a second opening to expose the implant for removal from the package.

20 Claims, 5 Drawing Sheets

(56) References Cited

U.S. PATENT DOCUMENTS

| | | | |
|---|---|---|---|
| 5,947,274 A * | 9/1999 | Taskis et al. | 206/204 |
| 6,050,400 A * | 4/2000 | Taskis et al. | 206/204 |
| 6,149,655 A * | 11/2000 | Constantz et al. | 606/94 |
| 6,622,864 B1 * | 9/2003 | Debbs et al. | 206/438 |
| 6,648,133 B1 * | 11/2003 | Blaschke et al. | 206/221 |
| 6,935,889 B2 * | 8/2005 | Picardo et al. | 439/521 |
| 7,040,485 B2 * | 5/2006 | Gupta et al. | 206/484.1 |
| 7,229,820 B2 * | 6/2007 | Wilson | 435/284.1 |
| 7,506,759 B2 * | 3/2009 | Iwatschenko | 206/438 |
| 7,594,577 B2 * | 9/2009 | Iwatschenko | 206/438 |
| 7,670,384 B2 * | 3/2010 | Kumar et al. | 623/23.63 |
| 2006/0108239 A1 * | 5/2006 | Iwatschenko | 206/63.5 |
| 2006/0280803 A1 | 12/2006 | Kumar et al. | |
| 2007/0074989 A1 * | 4/2007 | Merboth et al. | 206/438 |
| 2007/0074990 A1 * | 4/2007 | Merboth et al. | 206/438 |
| 2007/0077280 A1 | 4/2007 | Collinge et al. | |
| 2007/0092398 A1 * | 4/2007 | McDonald | 422/28 |
| 2008/0125721 A1 * | 5/2008 | Timm | 604/187 |
| 2008/0128296 A1 * | 6/2008 | Stopek et al. | 206/63.3 |
| 2009/0137042 A1 * | 5/2009 | Govil et al. | 435/395 |
| 2009/0209031 A1 * | 8/2009 | Stopek | 435/307.1 |

* cited by examiner

METHOD AND APPARATUS FOR REHYDRATION OF LYOPHILIZED BIOLOGIC MATERIALS

FIELD OF INVENTION

The invention relates to packaging and rehydration of biologic materials and/or medical devices.

BACKGROUND OF THE INVENTION

It is well known to repair soft tissue defects, such as hernia ruptures and the like, with implants that temporarily or permanently replace the damaged or missing tissue. Such implants may comprise sheets of woven polymeric materials or animal tissue, such as acellular human or porcine dermis. Examples of such products currently on the market include AlloMax™, which is an acellular human dermis surgical graft product, and Collamend™ FM, which is a fenestrated acellular porcine dermal collagen implant product, both products available from Davol, Inc., a subsidiary of C. R. Bard, Inc. of Warwick, R.I., USA.

Such implants often are packaged in a lyophilized condition (i.e., dehydrated) and must be rehydrated in the sterile surgical theater just prior to implantation. The implants also may be impregnated with antibiotics or other drugs that the implant will elute into the surrounding tissue after implantation.

The conventional processes for rehydrating such lyophilized implants leave much to be desired. In one technique, the implant is removed from its sterile packaging within the sterile surgical theater and placed in a sterile basin. A basin of appropriate size that fits the implant but does not require excessive amounts of saline (or other rehydration liquid) may not be available.

Then, a sufficient amount of the rehydration liquid is poured into the basin to submerge the implant therein. Many, if not most, implants float in saline. Hence, it frequently is necessary to place a sterile surgical instrument on top of the implant within the basin in order to keep it submerged in the rehydration liquid.

Furthermore, the amount of rehydration liquid placed in the basin is not well controlled and, in fact, if the basin is much larger than the implant, it may require an excessive amount of rehydration liquid just to submerge the implant. Particularly, often, an implant can become overhydrated by exposure to too much liquid or for too long a period of time. This is a particular issue, for instance, for antibiotic or drug eluting implants. Specifically, too much of the antibiotic may leach out of the implant while it is being rehydrated if it is placed in an excessive amount of rehydration liquid or left in the rehydration liquid for an excessive amount of time.

On the other hand, it also is possible to put too little rehydration liquid into the basin, resulting in under-hydration of the implant or an extended rehydration period.

Yet further, the rehydration process can be messy because the basin has a wide opening and it is easy to knock the basin about in the operating room, causing spillage, mess, and slippery floors, all of which could lead to problems during the surgery. In addition, spillage of liquid, particularly if it contains an antibiotic, may contaminate other sterile items on the operative field.

Further, the wide opening of the basin allows for evaporation of the rehydration liquid to occur freely. Evaporation is not typically a problem if the rehydration liquid is saline. However, it is not uncommon for the rehydration liquid to contain additives that may be highly volatile and may evaporate very quickly once exposed to the room air. Finally, if the basin is open on top, there is a potential that air-borne contaminants may settle on the implant.

Another common technique for rehydrating lyophilized implants is to package the implant along with a rehydration tray. The process is substantially similar to that described above in connection with the use of sterile basins, but using the tray supplied with the implant as a substitute for the basin. The implant is removed from its sterile packaging and placed in the tray supplied with the implant and the rehydration liquid is poured over it. The use of rehydration trays specifically provided with the implant typically eliminates the problem of the rehydration vessel being ill-sized for the particular implant. However, it still suffers from the same issues of spillage, evaporation, flotation of the implant, the potential for air-borne contaminants to settle on the implant, and poor control of the amount of rehydration liquid so that the implant may be either under-hydrated or over-hydrated. Even further, the trays are single-use disposable trays and thus are often very flimsy and, therefore, prone to spillage, dropping, dropping of the implant from the tray, breakage, and failure.

SUMMARY OF THE INVENTION

The present invention is a method and an apparatus for packaging lyophilized implants, biologic materials, and other medical implements that minimizes the possibility of under- or overhydration of the implant, prevents spillage of the rehydration liquid or implant, avoids the use of ill-sized rehydration vessels, and eliminates evaporation of the rehydration liquid. In accordance with one aspect of the invention, a lyophilized implant may be packaged for delivery to the surgical site in a sealed, flexible/expandable, sterile inner pouch. The inner pouch may be further packaged within an outer sterile package. The inner package contains a port, preferably a self-sealing needleless port through which rehydration fluid and/or other materials, such as medications or growth factors, may be introduced into the inner pouch via a needleless syringe without substantially opening the inner pouch. The pouch may be made of a foil or other flexible, but substantially non-stretchable, material so that the inner pouch can expand to accept only a predetermined amount of rehydration liquid, sufficient to reconstitute the lyophilized biologic implant material therein.

After rehydration for the desired amount of time, any remaining excess rehydration liquid within the pouch may be removed via the same port. The preferred embodiment would permit only the optimal volume of rehydration liquid to be added to the inner pouch.

Next, the inner pouch is opened via a different opening mechanism from the aforementioned rehydration port to expose the implant for removal from the package and implantation into the patient. The different opening may comprise a cover or other portion that is peelable or otherwise separable from the remainder of the pouch so as to provide a large enough opening to remove the implant from the pouch therethrough.

DESCRIPTION OF THE PREFERRED EMBODIMENTS

Figure 1:
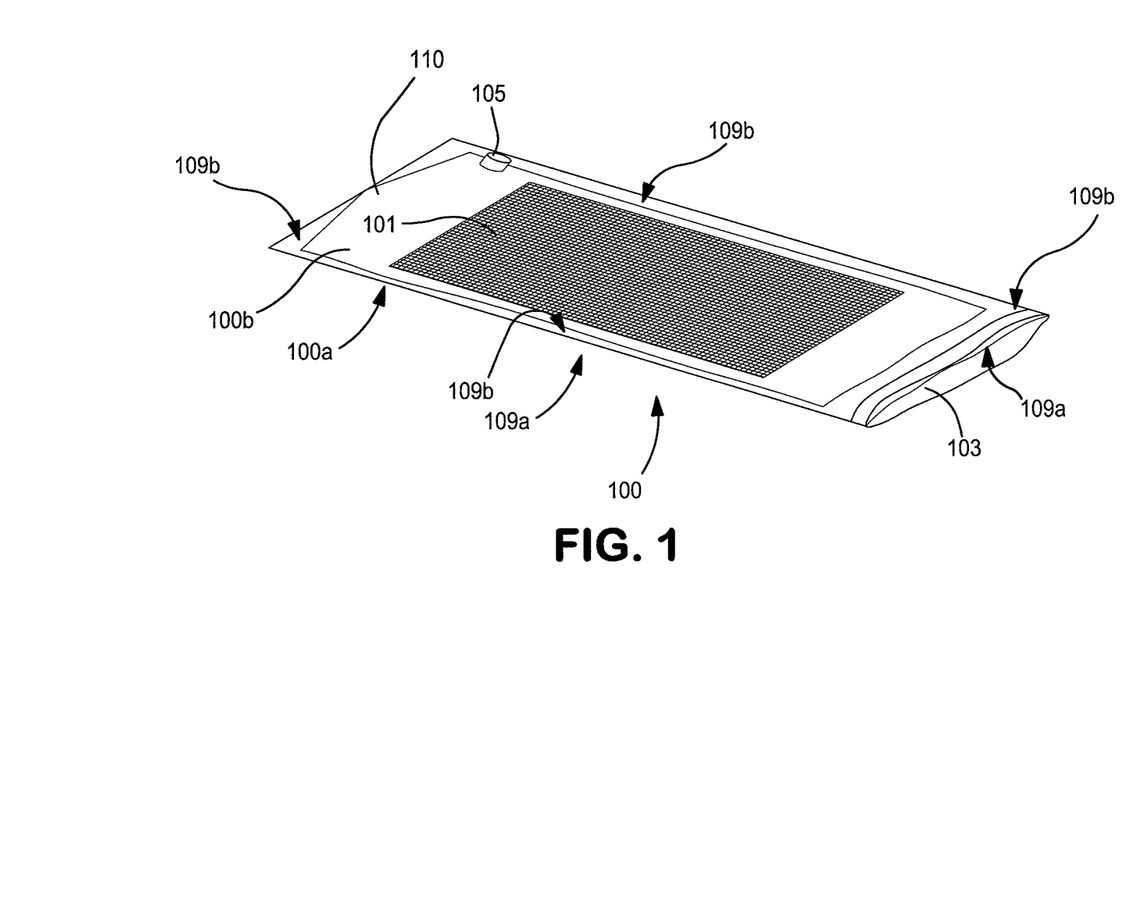
FIG. 1 is a perspective view of one illustrative embodiment of a sealed inner package for a lyophilized implant in accordance with the principles of a first embodiment of the invention.

FIG. 1 is a perspective view of a packaging method and apparatus for lyophilized implants in accordance with the principles of the present invention. The apparatus comprises a pouch 100 within which the lyophilized prosthesis or implant 101, such as prosthesis constructed of a biologic tissue material or mesh material, is contained. The pouch is shown as transparent in the drawing so that the implant 101 can be seen in the drawing for sake of clarity. However, this is not necessary and, in fact, it may be undesirable to allow the implant to be exposed to light.

In any event, the pouch 100 may be formed of a flexible, but substantially non-stretchable material, such as Mylar™ with Tyvek™. The pouch preferable bears gussets 103 so that it can be folded into a substantially flat configuration, but, upon introduction of a pressurized liquid into the sealed pouch, the pouch can be expanded to a predetermined size, and particularly, a predetermined internal volume.

A rehydration port 105 is provided for permitting rehydration liquid to be introduced to the internal volume of the pouch preferably without exposing the implant within the inner pouch. In one preferred embodiment, the port 105 is a needleless port such as is commonly used with IV (intravenous) bags. Such ports comprise a resilient self-sealing material, such as a thermoplastic elastomer. The tip of a syringe (with or without a needle) may be forced through the port 105 and into the internal volume of the container with the port material sealing around the tip of the syringe. When the syringe tip is removed, the port material seals around the hole previously formed by the tip of the syringe to return the port back to a sealed condition.

In other embodiments, the port may be as simple as a screw cap, press cap, or other resealable port, including a resealable plastic zipper type closure system (such as found on Ziploc™ plastic food storage bags). In yet other embodiments, the port may be in the form of a Luer taper connector, which is a basic friction fit commonly used in many industries, including pharmaceuticals and health care. The Luer taper connector may feature a locking ring for a more secure connection. See, for instance, Luer-Lock; ANSI standard HIMA MD70.1, ANSI/AAMI Taper Luered Fitting Standard: and ISO 594-1 standards, such as ISO 594-1:1986.

The pouch itself may be comprised of two components or pieces 100a, 100b of the pouch material edge-sealed to each other. A first piece 100a may be in the form of a tray bearing gussets 103 so that it can be folded substantially flat. The second piece 100b may be a flat sheet. The two pieces are attached to each other at their respective edges 109a, 109b. The sealing may be achieved via an adhesive bead 115 (see FIG. 4) or a heat activation seal around the edges of the pieces. This seal is separable and/or breakable and should allow the two pieces 100a, 100b to be peeled away from each other using hand strength so as to allow the medical staff to open the pouch to remove the implant 101 from the pouch after it is rehydrated, as discussed below. A tab, such as chevron shaped tab 110 may be provided on one or both components 100a, 100b of the pouch to provide a place to grip the pouch to pull the one component, e.g., 100a apart at the seal 115 from the other component, e.g., 100b to open the pouch and expose the implant for removal from the pouch 100.

In other embodiments, this second seal for opening the pouch for removal of the implant therefrom also may comprise a plastic zipper opening mechanism (like a Ziploc™ bag) or a weakened tearable strip (like a restaurant ketchup packet with serrated v-edges), or a perforated strip edge.

Figure 5:
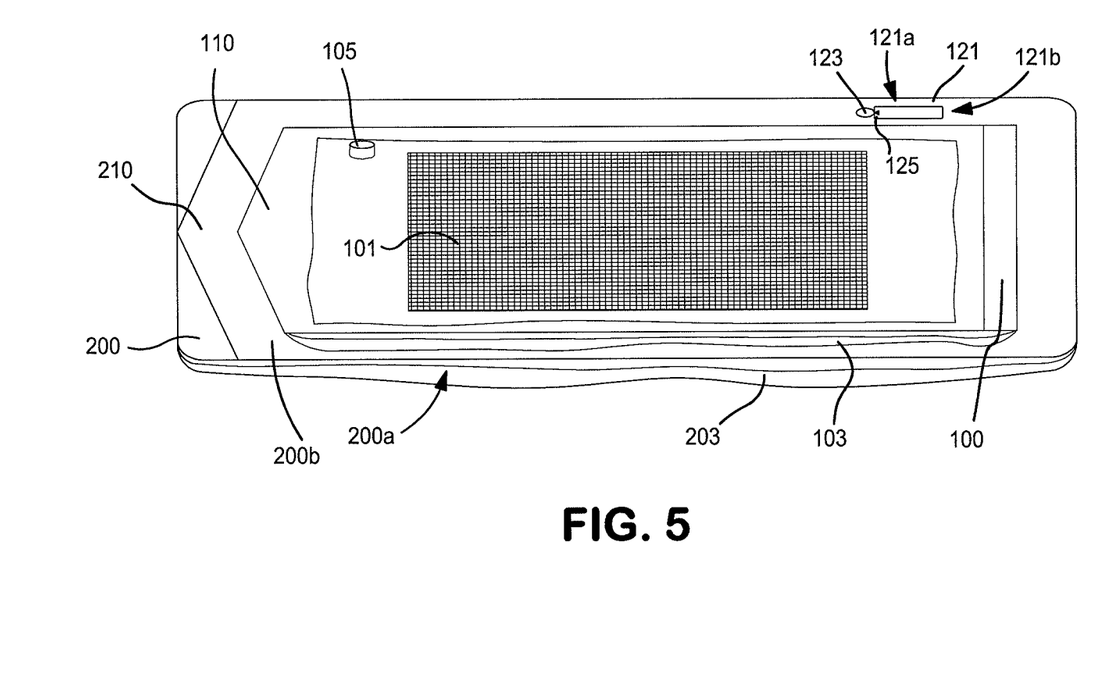
FIG. 5 is a perspective view of a second embodiment of the invention.

FIG. 5 illustrated yet another embodiment for applications in which it is desirable or at least optional to add another substance to the prosthesis or rehydration liquid during rehydration. The additional substance may, for instance, be an antibiotic drug, a medication, or a growth hormone. A vial or other additive container may contain the proper amount of such substance relative to the amount of rehydration liquid that can fit within the inner pouch when fully expanded to provide the desired concentration.

Referring to exemplary FIG. 5, the packaged product may be delivered with a vial 121 of the additional substance included in the overall packaging, such as enclosed within the outer pouch 200, and possibly attached to the outside of the inner pouch 100. The vial 121 can be opened, such as by breaking or tearing the vial or cutting the vial with a scissor or other cutting implement. Of course, one can mix the contents of the vial with the proper amount of rehydration liquid outside of the inner pouch 100, e.g., in a beaker, bowl, or other container, and then introduce the rehydration liquid containing the additive into the inner pouch 100 as previously described. However, in one preferred embodiment, the contents of the vial are poured into the inner pouch through the rehydration port 105 immediately before the rehydration liquid is introduced into the inner pouch (or possibly after some of the rehydration liquid has been introduced into the inner pouch 100, but before the pouch is fully expanded).

The contents of the vial may be in solid form (e.g., a powder) or liquid form.

In yet another embodiment best suited for vials with liquid contents, the contents of the vial may be withdrawn from the vial and introduced into the inner pouch by puncturing the vial with the needle of a syringe, withdrawing the contents with the syringe, and then injecting the contents into the inner pouch with the same syringe.

In another embodiment, the vial 121 may be attached to the outside of the inner pouch 100 via a breechable junction 123, such as a one-way valve (flow direction into the inner pouch) that has some minimum required pressure differential to open. In this manner, the doctor, nurse, or other personnel could simply squeeze the vial 121 just prior to, during, or after introduction of the rehydration fluid into the pouch to release the contents of the vial into the pouch.

In yet other embodiments, the junction 123 between the vial and the pouch may be any breakable barrier (e.g., puncturable) so that the inside of the vial 121 and the inside of the pouch 100 come into fluid communication with each other upon breakage of the junction 123. Such an embodiment may be desirable if the rehydration port 105 is in the form of a needleless port or other type of port through which it would be difficult or impossible to pour the contents of the vial into the pouch 100. Such a concern may be particularly acute if the contents of the vial are in powder or other solid form such that it cannot be injected through a needleless port. This may be accomplished, for instance, by sealing a part of the vial 121, e.g., the first longitudinal end 121a, to the surface of the inner pouch around the junction 123 and providing a sharp point 125 within the vial 121 adjacent the junction 123 that is sealed to the inner pouch 100, which point 125 can be used to puncture the inner pouch when desired. For instance, the first longitudinal end 121a of the vial 121 may be sealed to the pouch at junction 123 as described above while the second longitudinal end 121b (or any other part of the vial) is loosely adhered to the pouch 100 so that the second end 121b of the vial can be torn away from the pouch 100. When it is time to introduce the contents of the vial 121 into the pouch 100, the back end 121b of the vial 121 is tilted up relative to the pouch while the first end 121a is still attached to the pouch causing the sharp point 125 to puncture the pouch 100 at the junction within the area where the vial is sealed to the pouch. The seal between the pouch 100 and the vial 121 is broken so that the contents of the two become comingled, but the system is still sealed against the external environment. The vial may be squeezed if necessary to help force its contents into the inner pouch to better intermix its contents with the rehydration liquid in the inner pouch 100.

In use, the sterile pouch is delivered aseptically to the sterile operative field in a flattened condition, i.e., with the gussets 103 in a folded condition.

Figure 2:
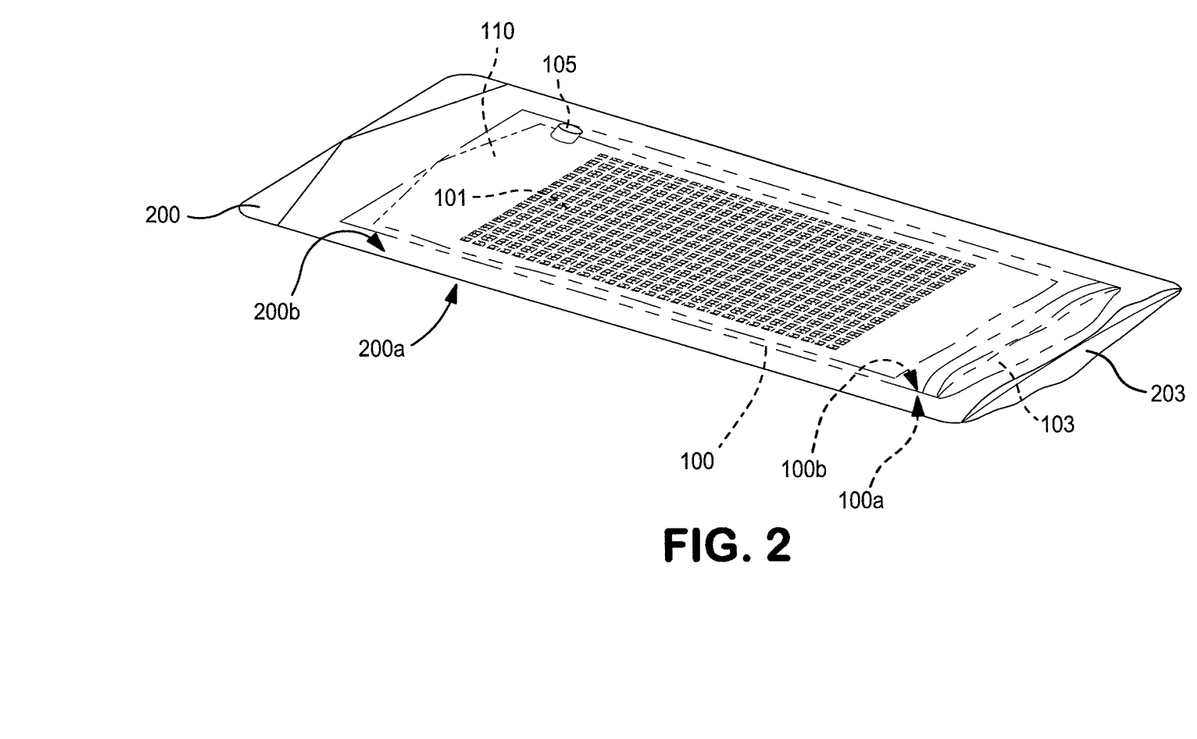
FIG. 2 is a partial see-through view of the inner package of FIG. 1 further packaged within an outer package in accordance with the principles of the invention.

In order to maintain the sterility of the pouch 100 when it is introduced into the sterile operative field, it may be packaged within a second, outer package at the manufacturing facility. The inner pouch (containing the also sterile implant) is sealed within the outer package at the manufacturing facility, and the inner and outer packages are sterilized by an acceptable method of sterilization. This is shown in FIG. 2, in which the inner pouch 100 is packaged within an outer pouch 200. The outer pouch 200 may be any reasonable packaging apparatus for maintaining the inside of the sealed outer package in a sterile condition until the outer packaging is opened within the operating room for delivery to the sterile operative field. The outer package 200 may be substantially similar to the inner pouch 100 in terms of material, manner of sealing, and construction (e.g., including a first component 200a, a second component 200b, and a second separable seal therebetween), but should be bigger than the inner pouch so that the inner pouch 100 can be entirely contained within the outer packaging package 200.

The outer packaging is opened aseptically in the operative environment and the inner pouch 100 is delivered aseptically to the sterile surgical field.

Figure 3:
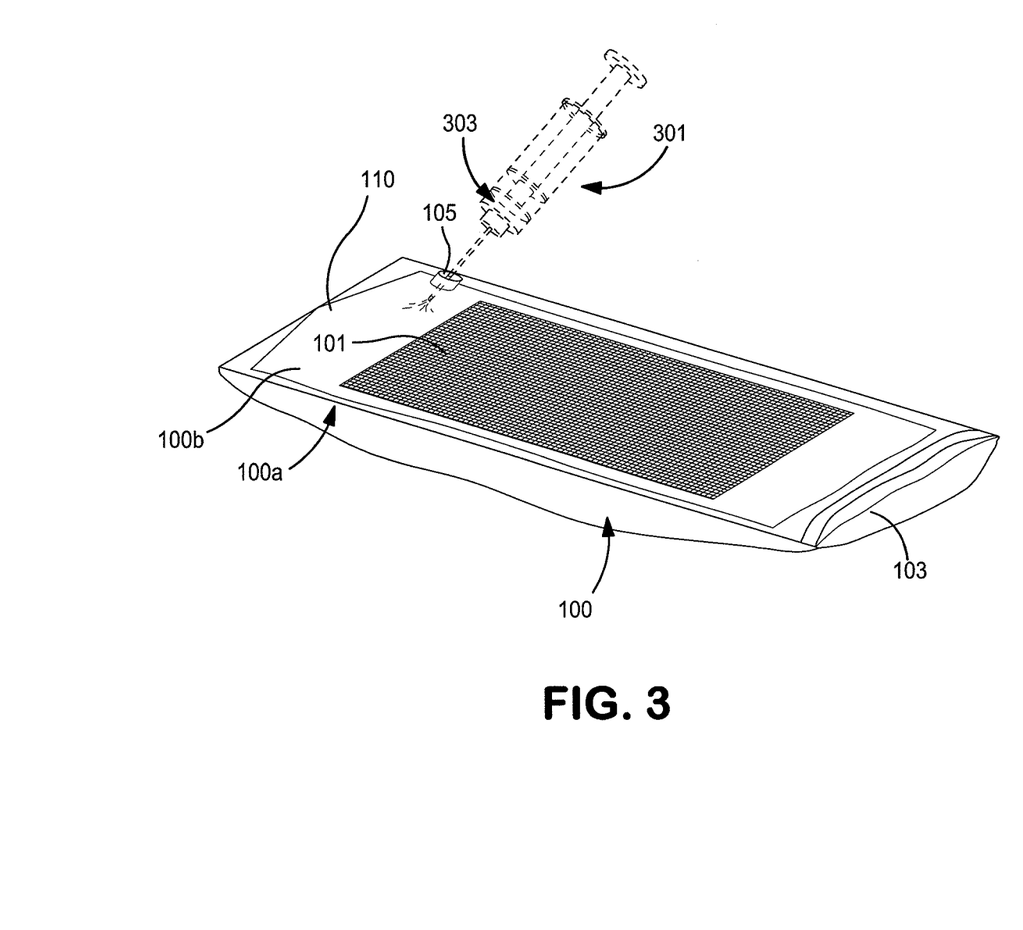
FIG. 3 is a perspective view of the inner package of FIG. 1 in its expanded configuration after the rehydration liquid has been introduced into its internal volume in accordance with the principles of the invention.

With reference to FIG. 3, at the appropriate time, the rehydration liquid is introduced into the internal volume of the pouch 100 through the rehydration port. For instance, in the needleless port embodiment illustrated in FIG. 3, the tip of a syringe 301 filled with the rehydration liquid 303 is inserted through the self sealing port 105 and the liquid 303 is injected into the internal space of the pouch. The rehydration liquid commonly comprises sterile saline. However, it may also contain or may have added to it growth factors, antibiotics, anti-coagulants or other medications or substances. Because the pouch is gusseted or otherwise expandable, the rehydration liquid will flow into the pouch and cause the pouch to expand, as shown (e.g., the gussets will unfold).

The configuration of the pouch, such as the configuration of the gussets, will allow the pouch to expand only to a predetermined internal volume, that volume preferably designed to allow the exact amount of rehydration liquid needed to properly rehydrate the implant to enter the pouch. After the pouch has fully expanded, the syringe is removed and the port resealed in accordance with its design. In the exemplary needleless port embodiment described herein, the port will self seal as soon as the syringe tip is removed from it.

In connection with the any of the embodiments such as discussed in FIG. 5 (in which a vial of additive substance is to be added to the prosthesis and/or rehydration liquid), the additive substance may be added to the pouch at this point. That may be performed in any of the manners discussed herein above. Alternately, also as previously noted, the additive may be added to the rehydration fluid externally of the pouch and the mixture added to the pouch.

The implant is then allowed to rehydrate for the amount of time specified by the manufacturer. At the end of that time, if there is any excess liquid still in the pouch (which, often, there will not be any liquid because the exact proper amount of rehydration fluid needed to rehydrate the implant was initially introduced into the pouch in accordance with the principles of the invention), any excess rehydration liquid may be removed via the rehydration port. For instance, in this embodiment, a syringe tip may be passed through the port and the plunger withdrawn to draw any excess liquid out of the pouch. A needleless approach is further beneficial because it minimizes the possibility of accidentally puncturing the pouch during introduction of the rehydration liquid into the pouch.

As another example, in a screw cap embodiment, the screw cap may be removed and any excess rehydration liquid simply may be poured out of the pouch. Whatever the form of the rehydration port, the opening created in it for adding or removing the rehydration liquid should be as small as reasonably possible and certainly small enough so that the implant cannot reasonably pass through it.

Figure 4:
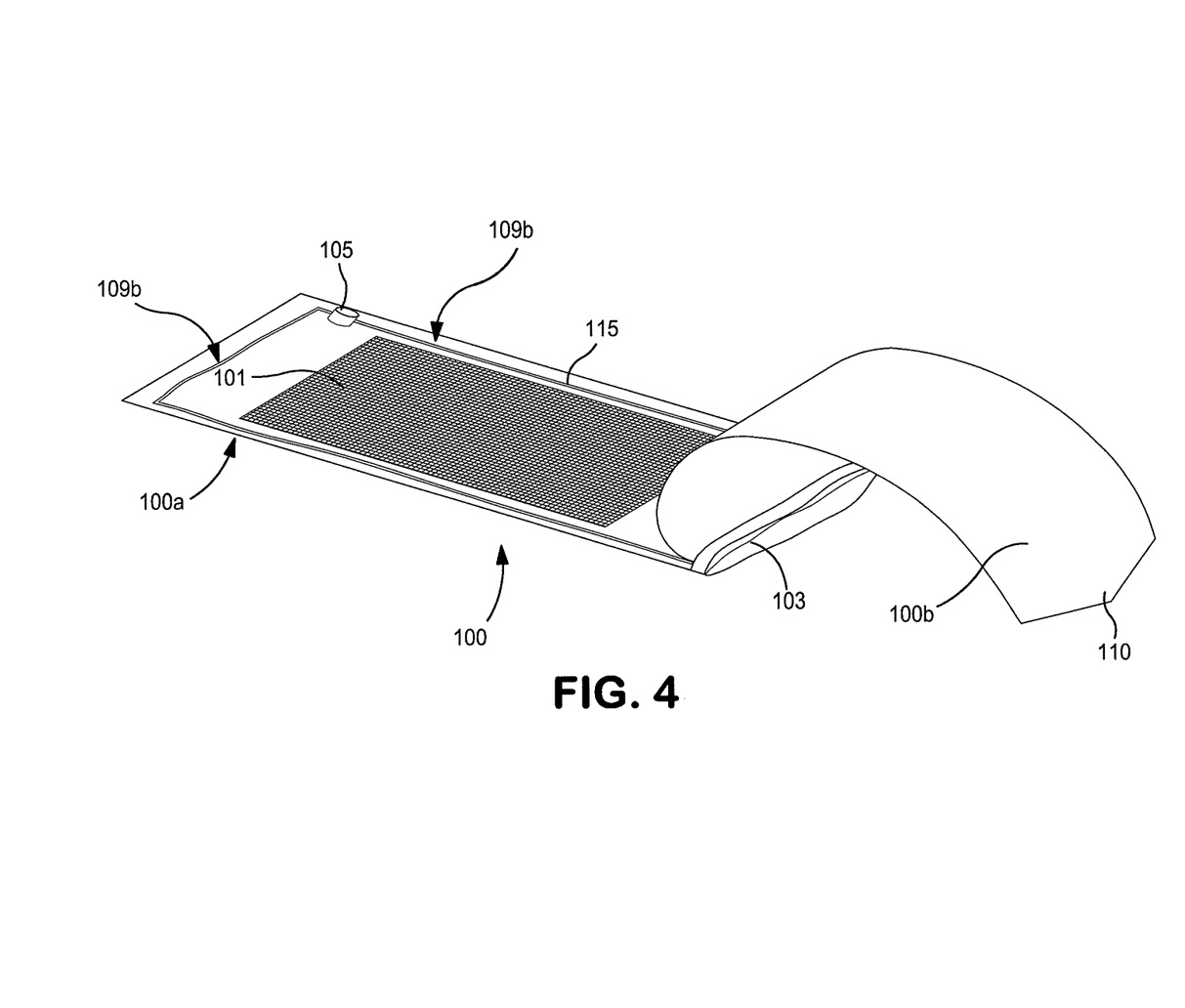
FIG. 4 is a perspective view of the inner package of FIG. 1 after it has been opened via the second opening in accordance with the principles of the invention to permit the implant to be removed therefrom.

Next, with reference to FIG. 4, the inner pouch is opened via the second opening mechanism. In this example, the tabs are grasped and pulled away from each other to tear the two pouch portions 100a, 100b apart from each other at the adhesive bead 115 or heat seal as previously described, thereby exposing the implant 101 for removal from the pouch for implantation.

Thereafter, the implant is removed and implanted in accordance with the particular surgical procedure.

The packaging and rehydration solution of the present invention maintains the implant in a substantially sealed sterile package until just prior to implantation. It also closely controls the amount of rehydration liquid that can be introduced to the implant. Specifically, it is virtually impossible to overhydrate because the pouch simply cannot accept more than a predetermined amount of rehydration liquid. Furthermore, it is difficult to underhydrate the implant because the pouch provides a simple tactile or visual cue as to when the pouch is fully filled. Essentially, one must introduce liquid until the pouch is fully expanded. In the needleless port embodiment, for instance, the person rehydrating the implant should keep injecting the rehydration liquid into the pouch until it becomes difficult to inject further liquid.

Furthermore, the packaging folds virtually flat before rehydration so that the product can be shipped and stored flat, thus saving transportation cost and shelf space during storage. Of course, the use of the packaging of the invention in connection with a substantially flat prosthesis is merely exemplary. The inventive packaging may be used to package any medical implement, including implants, prostheses, biologic materials, instruments, and devices, and is capable of being folded or other wise reduced in size and shape to substantially conform to the thing contained within it for minimal storage and shipping space. Yet further, the implant remains within a substantially sealed pouch during rehydration so that evaporation and contamination are avoided. Furthermore, because the pouch remains substantially sealed during the period of rehydration, the rehydration liquid cannot be spilled during this time. Furthermore, when the pouch is opened at the second opening for removing the hydrated implant, there should be no excess liquid within the pouch such that chances for spillage of rehydration liquid are even further diminished. Furthermore, there is no flotation issue because the implant remains within a sealed container during rehydration that contains nothing but the implant and rehydration liquid.

Having thus described a few particular embodiments of the invention, various alterations, modifications, and improvements will readily be obvious to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. An apparatus for hydrating a lyophilized medical implement comprising:
a lyophilized medical implement, the lyophilized medical implement intended to be properly hydrated with a certain volume of rehydration liquid;
a sealed container constructed of a flexible and substantially non-stretchable material, the sealed container comprising an expandable structure having a first state and a second state; and
a resealable port on the sealed container for receiving rehydration liquid therethrough into the sealed container; wherein:
in the first state, the sealed container has a first internal volume;
in the second state, the sealed container has a second internal volume that is a maximum internal volume of the sealed container, the sealed container being configured to have the maximum internal volume being predetermined to correspond to a combined volume of the lyophilized medical implement and the certain volume of rehydration liquid; and
the lyophilized medical implement is contained within the sealed container;
whereby, the sealed container facilitates proper hydration of the lyophilized medical implement by providing predetermined maximum internal volume that structural limits receipt of rehydration liquid to no more than the certain volume of rehydration liquid for properly hydrating the lyophilized medical implement.

2. The apparatus of claim 1 further comprising:
a breakable seal on the sealed container through which the lyophilized medical implement may be removed by the sealed container.

3. The apparatus of claim 1 wherein the resealable port comprises a needleless port.

4. The apparatus of claim 1 wherein the resealable port comprises a port that may be punctured at a point by a puncturing implement and that will reseal around the puncture point upon removal of the puncturing implement.

5. The apparatus of claim 2 wherein the sealed container comprises first and second container components sealed to each other via a first separable seal and wherein the breakable seal comprises the first separable seal.

6. The apparatus of claim 1 further comprising an outer package within which the sealed container is enclosed.

7. The apparatus of claim 6 wherein the outer package comprises first and second outer package components sealed to each other via a second separable seal and wherein the outer container may be opened via the second separable seal.

8. The apparatus of claim 1 wherein the lyophilized medical implement is one of a biologic tissue material or mesh material prosthesis.

9. The apparatus of claim 8 wherein the mesh material prosthesis is substantially flat.

10. The apparatus of claim 9 wherein the expandable structure of the sealed container comprises gussets that are expandable from a first compressed state in which the sealed container has the first internal volume to a second expanded state in which the sealed container has the second internal volume.

11. The apparatus of claim 1 wherein, in the first state, the sealed container may be shaped to conform substantially to a shape of the lyophilized medical implement contained therein.

12. The apparatus of claim 1 further comprising an additive container bearing an amount of an additive substance for incorporation into the rehydration liquid, the amount being determined as a function of the quantity of rehydration liquid that can fit within the second internal volume.

13. An apparatus for hydrating a particular lyophilized medical implement with a predetermined volume of rehydration liquid, the apparatus comprising:
a sealed container constructed of a flexible and substantially non-stretchable material, the sealed container comprising gussets expandable from a first compressed state in which the sealed container has a first internal volume, to a second expanded state in which the sealed container has a second internal volume, the sealed container being constructed so that the second internal volume is predetermined to correspond to a combined volume of (a) the particular lyophilized medical implement and (b) the predetermined volume of rehydration liquid, the second internal volume being a maximum internal volume of the sealed container;
the particular lyophilized medical implement contained within the sealed container; and
a resealable port on the container for receiving rehydration liquid therethrough into the sealed container.

14. The apparatus of claim 13, wherein the sealed container is substantially flat when the gussets are in the first compressed state.

15. The apparatus of claim 13, wherein the sealed container conforms substantially to a shape of the lyophilized medical implement contained therein when the gussets are in the first compressed state.

16. The apparatus of claim 13, wherein the sealed container conforms substantially to a shape of the medical implement contained therein when the gussets are not in the second expanded state.

17. The apparatus of claim 13, further comprising an additive container containing an amount of an additive substance for incorporation into the rehydration liquid, the amount being provided as a function of a quantity of rehydration liquid that can fit within the second predetermined internal volume.

18. An apparatus for hydrating a lyophilized medical implement comprising:
a sealed container constructed of first and second components constructed of a flexible and substantially non-stretchable material, the first component being a tray configured for receiving a medical implement, the second component being a sheet joined to the first component by a seal, the seal being breakable to permit removal of the medical implement;
a particular lyophilized medical implement contained within the sealed container; and a resealable port, disposed on one of the first and second components of the sealed container, for receiving rehydration liquid therethrough into the sealed container;

the tray comprising a plurality of gussets, the gussets having a first state in which the sealed container has a minimum internal volume, and a second state in which the sealed container has a maximum internal volume, the maximum internal volume being fixed and predetermined to correspond to a combined volume of the particular lyophilized medical implement and a maximum volume of rehydration liquid selected to avoid overhydration of the particular lyophilized medical implement.

19. The apparatus of claim 18 further comprising an outer package enclosing entirely the sealed container, the outer package comprising a first outer package component and a second outer package component sealed to the first outer package component via a second seal, the second seal permitting manual separation of the second outer package component from the first outer package component to permit removal of the sealed container from the outer package.

20. The apparatus of claim 19, wherein at least one of said first and second outer package components comprises a chevron-shaped pull tab, and wherein said second seal permits the second outer package component to be peeled away from the first outer package component using hand strength.

* * * * *